United States Patent [19]
Bellon et al.

[11] Patent Number: 5,928,484
[45] Date of Patent: Jul. 27, 1999

[54] SEPARATION PROCEDURE FOR LP(A) BY MEANS OF ELECTROPHORESIS, GELS FOR THE IMPLEMENTATION OF THIS PROCEDURE, AND APPLICATION TO THE IN VITRO DETERMINATION OF THE ATHEROGENIC RISK ASSOCIATED WITH THE PRESENCE OF LP(A)

[75] Inventors: Franck Bellon, Issy Les Moulineaux; Aline Bringard, Lisses, both of France

[73] Assignee: Sebia, Issy Les Moulineaux, France

[21] Appl. No.: 08/676,884

[22] Filed: Jul. 5, 1996

Related U.S. Application Data

[63] Continuation of application No. 07/986,775, Dec. 8, 1992, abandoned.

[30] Foreign Application Priority Data

Dec. 11, 1991 [FR] France ................................... 91 15387

[51] Int. Cl.⁶ .................... G01N 22/26; G01N 27/447
[52] U.S. Cl. ...................... 204/469; 204/456; 204/466
[58] Field of Search .................. 204/458, 461, 204/466, 467, 468, 469, 456

[56] References Cited

FOREIGN PATENT DOCUMENTS

| 8202599 | 8/1982 | WIPO . |
| 8900689 | 1/1989 | WIPO . |

OTHER PUBLICATIONS

American Journal of Human Genetics: vol. 49, No. 5, Nov. 1991, Chicago, USA, pp. 1063–1074; Kamboh M.I. et al.: 'Expressed hypervariable polymorphism of apolipoprotein(a)' p. 1064, colonne de droite, ligne 22—p. 1066, colonne de gauche, ligne 19.

Electrophoresis: vol. 7, No. 5, May 1986, Weinheim, Germany pp. 197–203; Boersum T. et al.: 'Electrophoretic migration velocity of amphiphilic proteins increases with decreasing Triton X–100 concentration: A new characteristic for their identification'.

Journal of Biological Chemistry: vol. 257, No. 1, Jan. 10, 1982, Baltimore US pp. 501–507; Gutermann et al.: 'Genetic variants of group A apolipoproteins'.

Clinica Chimica Acta: vol. 188, No. 1, No month available 1990, Amsterdam, NL, pp. 71–77; Bruckert E. et al.: 'Does electrophoresis reliably screen for high serum lipoprotein(a)?'.

Noble, R., "Electrophoretic Separation of Plasma Lipoproteins in Agarose Gel", *Journal of Lipid Research*, 9:693–700 (1968).

C. Desreumaux et al, "Analyse des lipoproteines par electrophorése surgel de polyacrylamide et par precipitation fractionnée à l'aide de polyanions. et de détergents." Ann. Biol. Clin. 34 No month available (1976)309–316.

Philippe Gambert et al, Cholestrol Gas–Liquid Chromatographic Micro–assay in Serum Lipoproteins Separated by Polyacrylamide Gel Electrophore Clinica Chimica Acta 100 No month available (1980) 99–105.

C. Desreumaux et al, "Fractionation of serum lipoproteins by preparative electrophoresis in polyacrylamide gel" Journal of Chromatography 130 (Jan. 1977) 336–341.

G. Utermann and W. Weber, "Protein composition of Lp(A) lipoprotein from human plasma" FEBS Letters, vol. 154, No. 2, (Apr. 1983) 357–361.

C. Desreumaux et al, "Analyse des lipoprotéines par électrophorèse sur gel de. polyacrylamide et par précipitation fractionée à l'aide de polyanions et de détergents" annales de Biologic Clinique No month available (1976) 309–316.

G. Utermann and W. Weber "Protein composition of Lp(A) lipoprotein from human plasma" FEBS Letters, vol. 154, No. 2 (Apr. 1983) 357–361.

S. Moulin, J.C. Fruchart, P. Dewailly, and G. Sezille, "Electrophorese Des Lipoproteines Seriques Plaque De Gel D'Acrylamide–Agarose, En Gradient Discontinu D'Acrylamide" Clinica Chimica Acta, vol. 91, No. 2 (Jan. 1979) 159–163.

Philippe Gambert, Christian Lallemant, and Prudent Padieu "Cholesterol Gas–Liquid Chromatographic Microassay In Serum Lipoproteins Separated By Polyacrylamide Gel Electrophoresis" Clinicu Chimica Acta, vol. 100/2 No month available (1980) 99–105.

*Primary Examiner*—William H. Beisner
*Assistant Examiner*—John S. Starsiak, Jr.
*Attorney, Agent, or Firm*—Merchant, Gould, Smith, Edell, Welter & Schmidt, P.A.

[57] ABSTRACT

The invention relates to a separation procedure for Lp(a) and the various lipoproteins contained in a biological sample by electrophoresis. The present invention is characterized in that the electrophoretic migration of the lipoproteins is carried out under conditions such that the electrophoresis gel and/or the above-mentioned biological sample contains compounds capable of modifying the electrophoretic mobility of Lp(a) differentially with respect to that of the other lipoproteins.

16 Claims, 6 Drawing Sheets

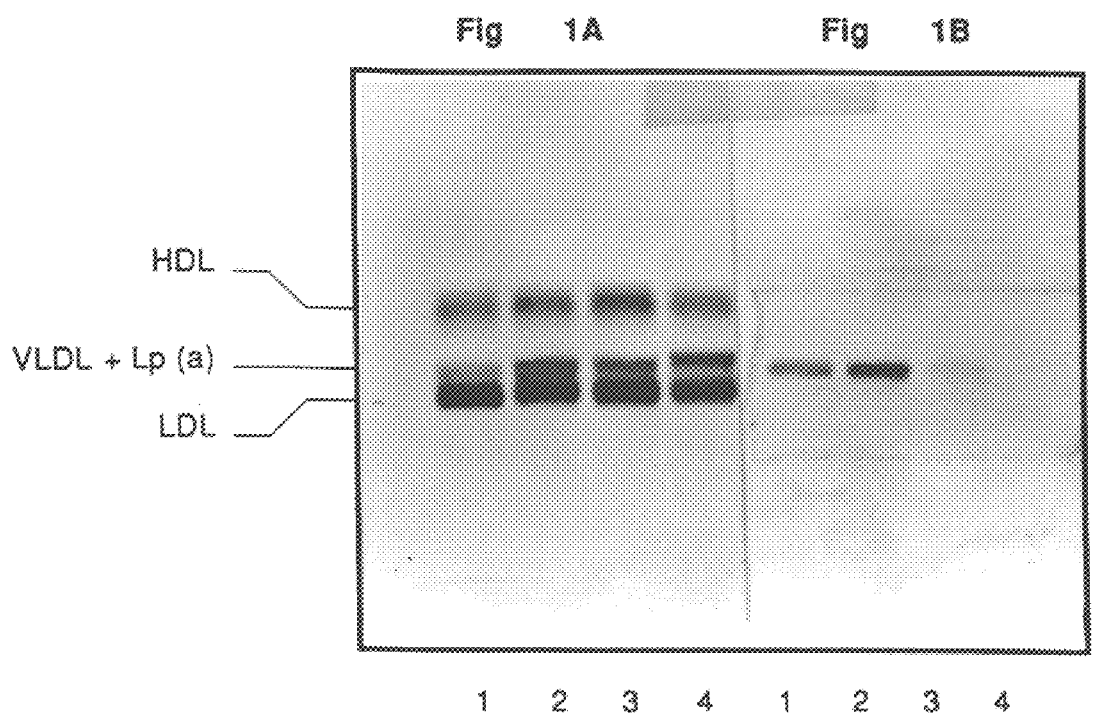

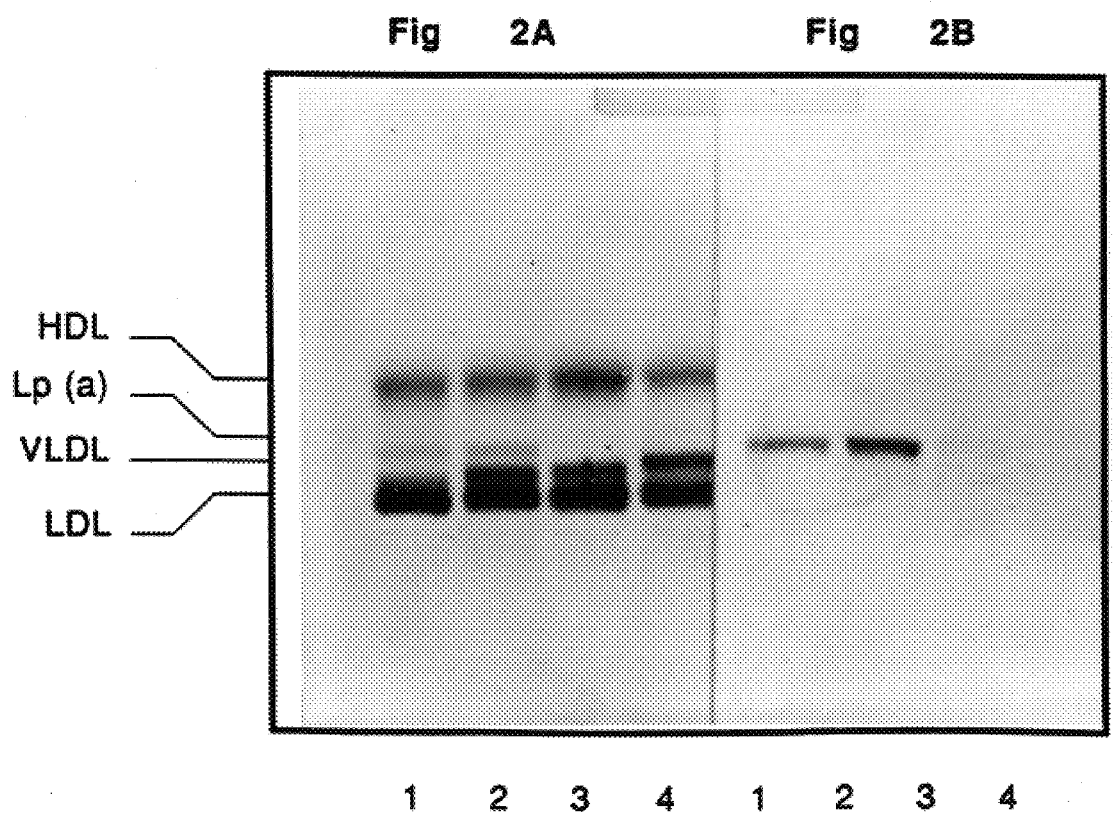

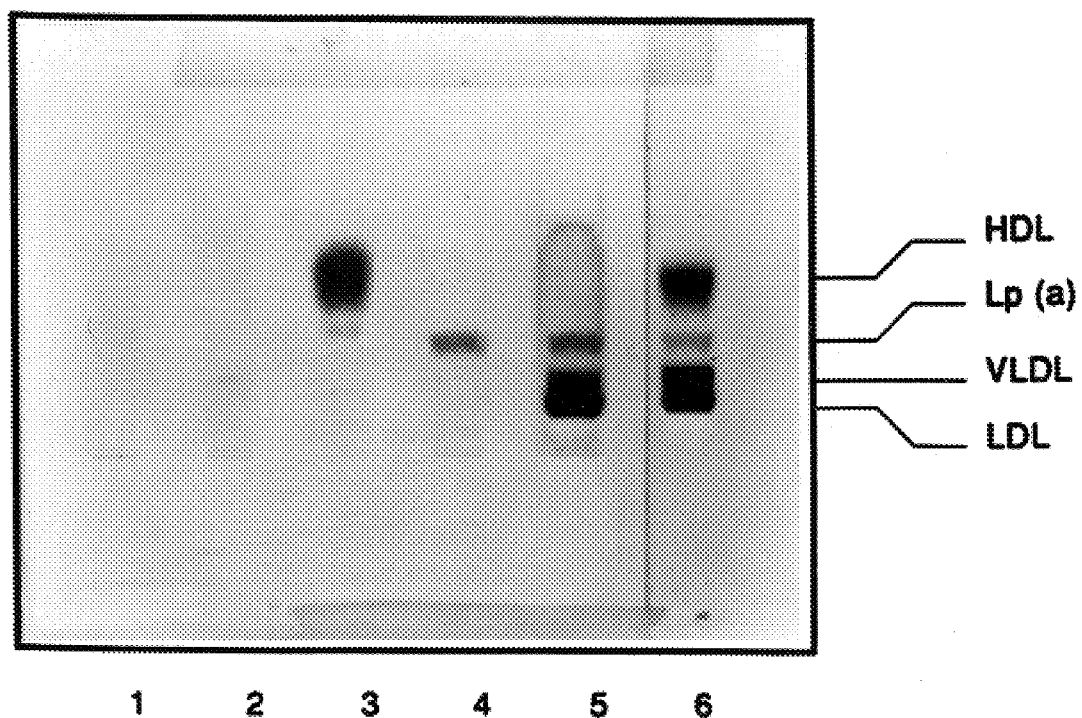

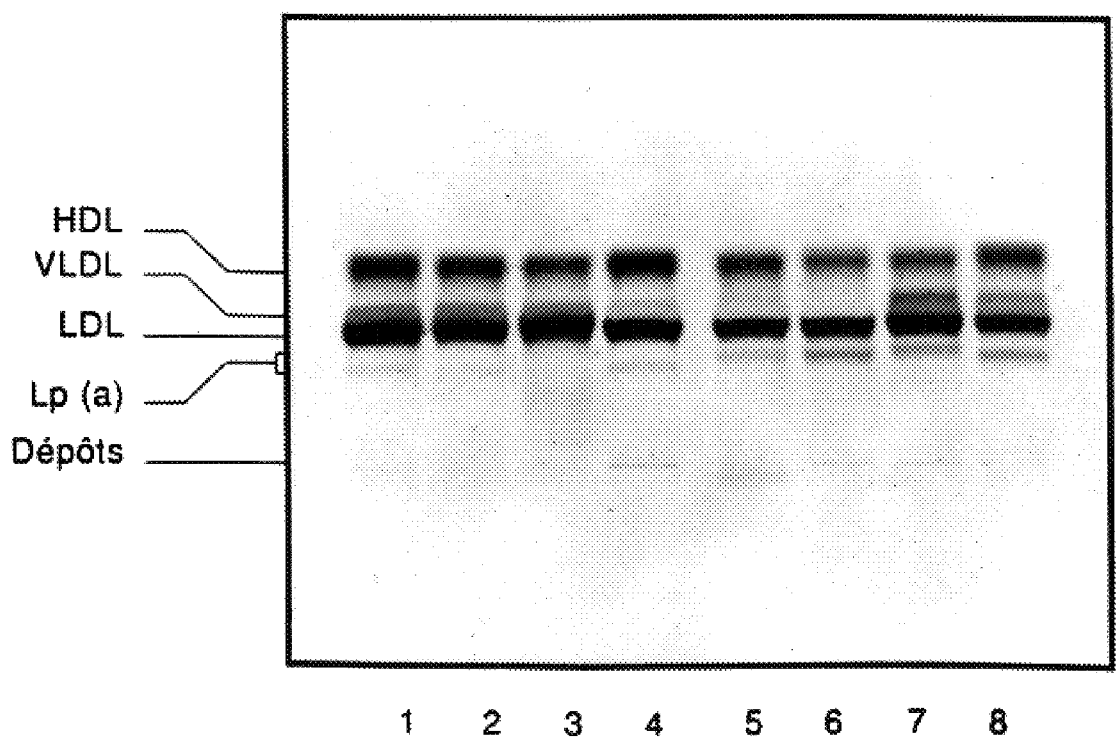

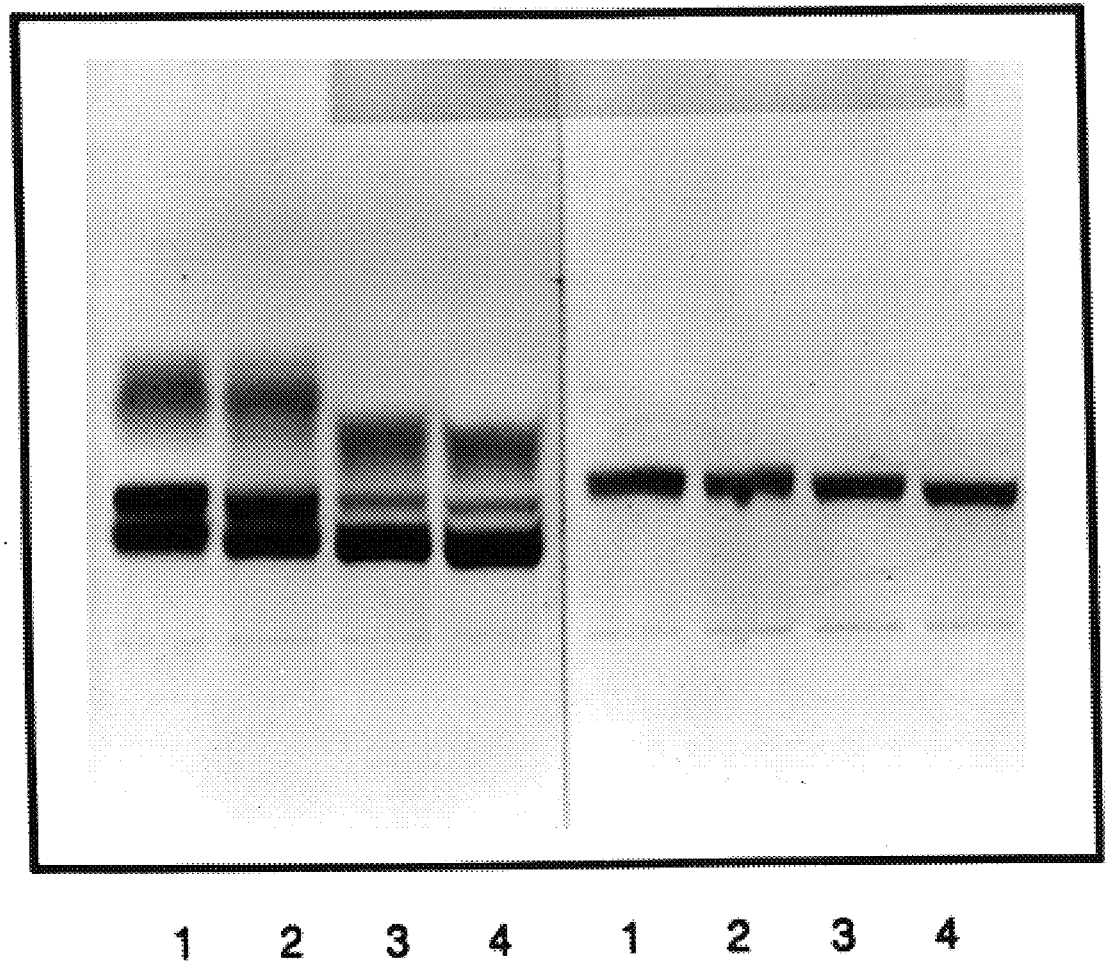

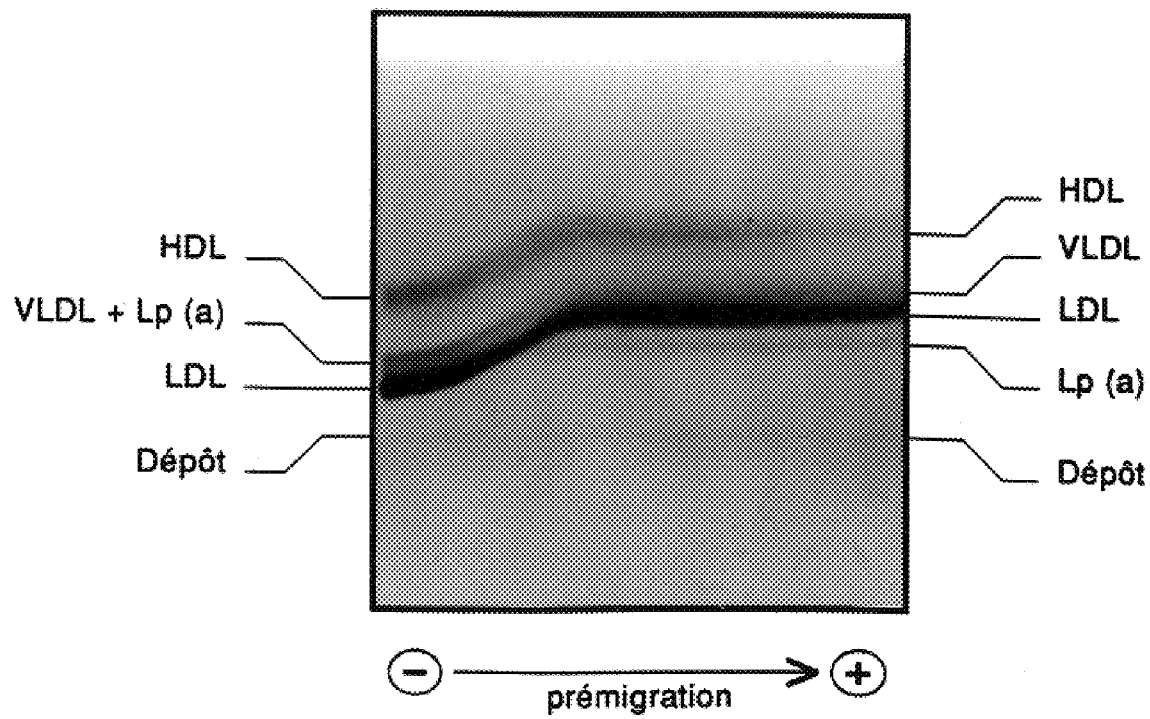

SEPARATION PROCEDURE FOR LP(A) BY MEANS OF ELECTROPHORESIS, GELS FOR THE IMPLEMENTATION OF THIS PROCEDURE, AND APPLICATION TO THE IN VITRO DETERMINATION OF THE ATHEROGENIC RISK ASSOCIATED WITH THE PRESENCE OF LP(A)

This is a continuation of application Ser. No. 07/986,775, filed Dec. 8, 1992, now abandoned.

BACKGROUND OF THE INVENTION

1. Field of the Invention

The subject of the present invention is a separation procedure for Lp(a) by means of electrophoresis, gels for the implementation of this procedure, as well as the application of this procedure to the determination of the atherogenic risk associated with the presence of Lp(a) and more particularly of the risks which an individual presents being affected by a disease such as atherosclerosis or any other disease associated with the latter.

2. Prior Art

The electrophoresis of human serum or plasma in agarose gel, followed by specific staining of the lipids, makes it possible to separate and visualize the different lipoprotein fractions, HDL, VLDL, LDL and chylomicrons, the levels of each of which are valuable indicators of the risks of atherosclerosis (FREDRICKSON et al., 1967, New Engl. J. Med., 276).

"Lp(a)" is a specific lipoprotein, identified by BERG in 1963 (Acta Pathol. Microbiol. Scand., 59, 369). It possesses a great structural similarity to the LDLs, but is characterized by an additional protein moiety, called apo(a), linked to the apo B100 by means of disulfide bridges.

Although the physiological role of Lp(a) has not been completely elucidated, many clinical studies have shown that a high level of plasma Lp(a) (higher than 0.3 g/l) constitutes an independent risk factor for atherogenesis (KOSTNER et al., 1981, Atherosclerosis, 38, 51; RHOADS et al. 1986, J. Ann. Med. Assoc., 256, 2540).

At present, classical electrophoresis of human serum or plasma (standard gel: 0.5% agarose, in Tris Veronal buffer; see FIG. 1A), usually allows the resolution of three lipoprotein fractions: the HDL (position $\alpha$), the VLDL (position pre$\beta$) and the LDL (position $\beta$). The lp(a) fraction, when it is present, migrates to the pre$\beta$1 position, and, it usually cannot be adequately distinguished from the VLDL for its presence or absence to be concluded with certainty in the context of the determination of the atherogenic risk associated with the presence of Lp(a) (BRUCKERT et al., 1990, Clin. Chim. Acta, 188, 71).

Consequently, the different methods for the detection and analysis of plasma Lp(a) are, at present, all based on the use of specific antibodies. More particularly, these methods are the following: immunonephelometry (CAZZOLATO et al., 1983, Clin. Chim. Acta, 135, 203), electrosyneresis (MOLINARI et al., 1983, Clin. Chim. Acta, 128, 373), electroimmunodiffusion according to LAURELL (KOSTNER et al., 1981, Atherosclerosis, 33, 51), the ELISA immunoenzymatic procedures (ABE et al., 1988, Clin. Chim. Acta, 177, 31), as well as an immunolatex procedure (VU DAC et al., 1985, J. Lipid. Res., 26, 267).

However, these assays are usually expensive, and are not systematically prescribed by the clinician in the context of dyslipoproteinemia research. Prior to such an assay, it would thus be very interesting to be able to detect the presence of Lp(a) in pathological amounts during a routine lipoprotein analysis.

One of the aims of the present invention is precisely that of placing at the disposition of clinicians a procedure for the separation of Lp(a) from the other lipoproteins of the serum, the cost of which is markedly lower than that of the present procedures, and which consequently may be prescribed in the context of routine dislipoproteinemia research.

The object of the present invention is also to make possible the detection of Lp(a) in a reliable manner and, as a consequence, the reliable in vitro diagnosis of the risk of appearance in an individual of diseases associated with atherosclerosis.

SUMMARY OF THE INVENTION

The invention relates to a procedure for the separation of Lp(a) and various lipoproteins contained in a biological sample by means of electrophoresis, characterized in that the electrophoretic migration of the lipoproteins is accomplished under conditions such that the electrophoresis gel and/or the above-mentioned biological sample contains compounds capable of modifying the electrophoretic mobility of Lp(a) differentially with respect to that of the other lipoproteins.

The above-mentioned procedure is more particularly characterized in that it enables the systematic separation in a biological sample of the Lp(a) fraction from the VLDL and LDL fractions, preferably while preserving the separation of the HDL, LDL and VLDL.

BRIEF DESCRIPTION OF THE DRAWINGS

FIGS. 1A and 1B

The FIGS. 1A and 1B represent a lipidogram obtained on a reference gel (not containing a compound capable of modifying the electrophoretic mobility of Lp(a) differentially with respect to that of the other lipoproteins) of 0.5% agarose, the migration buffer used being the following:

0.06M Tris, 0.01M Veronal, 0.05M Veronal sodium salt, BSA 1 g/l.

In the 2 left lanes (lanes 1 and 2), the sera deposited possess a pathological Lp(a) level. In the 2 right lanes (lanes 3 and 4), the sera deposited have a zero or very low level of Lp(a).

FIG. 1A shows the revelation of the lipoproteins with Sudan Black.

FIG. 1B shows immunofixation with a specific antiserum directed against Apo(a) and makes it possible to demonstrate Lp(a) in lanes 1 and 2 which is not visible in the lipidogram of FIG. 1A, because Lp(a) is superposed on the VLDL fraction.

FIGS. 2A and 2B

The FIGS. 2A and 2B represent a lipidogram obtained on a gel of the invention containing 0.03M of magnesium acetate (the buffer is identical with that described in FIG. 1A). The same sera are used on these gels as on FIGS. 1A and 1B and in the same positions.

FIG. 2A shows the revelation of the lipoproteins with Sudan Black.

In the lanes 1 and 2 of FIG. 2A, the presence of a band is seen which did not appear on FIG. 1A and which corresponds to Lp(a).

FIG. 2B shows immunofixation with a specific antiserum directed against Apo(a) and confirms the revelation of Lp(a), which is also apparent in FIG. 2A.

FIG. 3

FIG. 3 represents a lipidogram obtained with a gel identical with that shown in FIGS. 2A and 2B, under conditions for migration identical with those used in the context of FIGS. 2A and 2B.

A serum possessing a pathological level of Lp(a) was loaded onto the 6 lanes.

In the lanes 1 to 5, immunofixations were carried out with the following antisera:

lane 1: anti-apoE lane 2: anti-apoCIII lane 3: anti-apo Al lane 4: anti-apo(a)

lane 5: anti-apoB lane 6: the staining of the lipoproteins has been carried out with Sudan Black.

It is observed that Lp(a) (constituted of apo(a) and apoB) is separated from the VLDL and LDL, and is not degraded.
FIG. 4

FIG. 4 shows a gel containing 0.026M I-hydroxy naphtalene 2-carboxylic acid. Eight different sera were loaded containing levels of Lp(a) varying from 0 to 0.7 g/l.

Migration occurred at 50 V for 45 mn. The revelation of the lipoproteins was carried out with the aid of Sudan Black.

Lp(a) can be seen to be present situated behind the LDL fraction and well differentiated.
FIGS. 5A and 5B FIGS. 5A and 5B show a gel such as that defined in FIG. 1A on which have been loaded the following four samples:

lane 1: untreated serum lane 2: serum treated with $10^{-3}$M Triton X-100 lane 3: serum treated with $10^{-3}$M Tween 20 lane 4: serum treated with $10^{-3}$M BRIJ 35.

Electrophoresis was carried out under the conditions described with respect to FIG. 1A.

In FIG. 5A, the lipoproteins were stained with Sudan Black.

In FIG. 5B, immunofixation was carried out with a specific antiserum directed against Lp(a).

It is observed that the neutral detergents have a retarding effect on the lipoproteins, Lp(a) being much less affected than the other lipoprotein fractions.
FIG. 6

FIG. 6 shows the electrophoresis of a serum containing Lp(a) in a gel in which the left half contains a molecule which has a hydrophobic moiety and is negatively charged (1-hydroxy naphtalene 2-carboxylic acid) and in which the left half does not contain this compound and thus this half corresponds to a reference gel.

The experiment shows directly the effect of 1-hydroxy naphtalene 2-carboxylic acid on the different lipoprotein fractions: the HDL, VLDL and LDL are markedly accelerated, whereas Lp(a) retains approximately the same mobility.

DESCRIPTION OF THE PREFERRED EMBODIMENTS

A particularly advantageous procedure of the invention is characterized in that the compound capable of modifying the electrophoretic mobility of Lp(a) differentially with respect to that of the other lipoproteins is selected from cations or cation complexes, the molecules having a hydrophobic moiety and being negatively charged or neutral surfactants.

According to a particularly advantageous embodiment of the procedure of the invention, the compounds capable of modifying differentially the electrophoretic mobility of Lp(a) with respect to that of the other lipoproteins are incorporated into the electrophoresis gel used. This is advantageously the case with cations.

According to another particularly advantageous embodiment of the procedure of the invention, the compounds capable of modifying differentially the electrophoretic mobility of Lp(a) with respect to that of the other lipoproteins, and more particularly the molecules having a hydrophobic moiety and being negatively charged or which are neutral surfactants, are introduced into the biological sample before standard gel electrophoresis is performed.

Preferably, the molecules having a hydrophobic moiety and being negatively charged which are capable of being added to the biological sample, are more particularly those characterized in that they have surfactant properties.

According to another mode of embodiment of the invention, the gels of the invention can also be prepared from standard gels modified by penetration of the charged substances, anionic or cathodic, incorporated beforehand into the migration buffer. This incorporation is carried out either during an electrophoretic step prior to the loading of the samples (pre-electrophoresis) (the loading being made either in the area of the gel into which the charged compounds have penetrated, or close to this area), or during the actual electrophoresis.

The charged compounds, whether anionic or cationic, can be incorporated equally well in the anode or cathode buffers or only into the cathode buffer in the case of the anionic compounds and only into the anode buffer in the case of the cationic compounds.

When the loading of the sample (biological material) is carried out in an area of the gel into which the cationic or anionic compounds have penetrated as a result of the pre-electrophoresis step, the lipidogram obtained is identical with that which would be produced in a gel had these cationic or anionic compounds been introduced directly during the pouring of the gel.

On the other hand, if the loading of the samples is performed in an area of the gel which these cationic or anionic compounds have not yet reached, it being understood that the lipoproteins of the sample will be brought into contact with these cationic or anionic compounds during the actual electrophoretic migration of these samples, the profile obtained on the lipidogram will be the result of the separation obtained on a standard gel and the separation obtained in a gel modified according to the invention. The closer the loading of the sample, carried out after the pre-electrophoresis step, is performed to the front of the zone of the gel into which these cationic or anionic compounds will have penetrated as a result of the pre-electrophoresis step, the more similar will be the profile of the lipidogram which would be obtained on a gel which the cationic or anionic compounds are present.

The addition of these compounds to the gel or the biological sample modifies differentially the electrophoretic mobility of Lp(a) with respect to that of the other lipoproteins.

The cations or cationic complexes or the neutral surfactants possess the property of slowing the rate of electrophoretic migration of the lipoproteins with respect to the rate of migration of those same lipoproteins on a standard electrophoresis gel not containing these cations or cationic complexes or these neutral surfactants. However, the rate of migration of Lp(a) is retared less than that of the other lipoproteins, or is even unmodified with respect to that obtained in a gel not containing cations or cationic complexes or neutral surfactants.

If it is considered, in the case of a given lipoprotein, that $d/d_T$ represents the ratio between the distance of migration in the gel containing the compound and the distance of migration in the reference gel for this same lipoprotein, and since the Lp(a) fraction is discrete if the distance from its nearest neighbouring fraction (namely VLDL) is at least 3 mm, the retardation factor $(d/d_T)$ of the VLDL fraction characterizing the procedures of the invention utilizing cations or cationic complexes or neutral surfactants is less than or equal to 0.7.

Regarding the molecules which have a hydrophobic moiety and are negatively charged they possess the property of accelerating the rate of electrophoretic migration of the lipoproteins with respect to the rate of migration of these same lipoproteins in a standard electrophoresis gel not containing these negatively charged molecules. As for Lp(a), its rate of migration is not appreciably changed by the presence of a molecule of the above-mentioned type.

Consequently, always assuming that the Lp(a) fraction is discrete if the distance from its nearest neighbouring fraction (namely LDL) is at least 3 mm, the acceleration factor $(d/d_T)$ of the LDL fraction characterizing the procedures of the invention using molecules which have a hydrophobic moiety and are negatively charged, is at least on the order of 2.3.

As seen previously, the rate of migration of the lipoproteins in the gel is diminished in the presence of cations or cationic complexes; since Lp(a) is less retarded than the other lipoproteins, under these conditions it becomes a markedly discrete band in the gel. On the lipidogram of FIG. 2A, the presence of an additional fraction between the VLDL and the HDL thus characterizes Lp(a). This additional fraction was identified unambiguously by means of immunofixation: the lipoprotein band in question is revealed by specific antibodies directed against the apolipoproteins apoB and apo(a) whereas it does not react with the anti-apo-AI, -apo-AII, -apo-CIII and -apo-E (FIG. 3).

A particularly advantageous procedure in the context of the present invention is characterized in that the compound capable of modifying the electrophoretic mobility of Lp(a) differentially with respect to that of the other lipoproteins is selected from cations or cationic complexes, the hydroxides of which are not precipitated or are partially precipitated at a pH of about 8 to about 9, such that there are at least $10^{-3}$ moles/l of unprecipitated cations or cationic complexes in the gel for electrophoresis.

Preferably, the cations used in the context of the present invention have an oxidation state higher than or equal to 2.

Advantageously, the cations are selected from the columns IIa, IIIa and IIIb of Mendeleev's table.

Such cations are advantageously selected from $Mg^{2+}$, $Ca^{2+}$, $Ba^{2+}$, $Sr^{2+}$, $Mn^{2+}$, $Be^{2+}$, $Al^{3+}$, $La^{3+}$, $Ce^{3+}$, $In^{3+}$ and $Y^{3+}$.

The cation used is preferably $Mg^{2+}$.

The cationic complexes used in the context of the present invention are advantageously selected from $NH_4^+$, $(NH_4^+)_2Fe^{2+}$, $NH_4^+Fe^{3+}$.

The concentration of the cations or cationic complexes in the gel is advantageously on the order of $10^{-3}$ to $10^{-1}$M, and preferably on the order of $5.10^{-3}$ to $3.10^{-2}$M. The effect observed on the separation of Lp(a) and the other lipoproteins is enhanced by increasing the concentration of the cations or cationic complexes. However, the incorporation of too large a quantity of salt (above $10^{-1}$M, or even 0.06M) is not desirable because this increases the migration time required and impairs the separation of the VLDL and LDL fractions.

The anion forming the salt with these cations or cationic complexes in solution does not play a role in the observed separation effect of Lp(a) and the other lipoproteins (chloride, acetate sulfate . . . ).

Another particularly preferred procedure of the invention is characterized in that the compound capable of modifying the electrophoretic mobility of Lp(a) differentially with respect to the other lipoproteins is a molecule which has a hydrophobic moiety and is negatively charged.

Preferably, the molecule which has a hydrophobic moiety and is negatively charged, . is either included in the class of anionic surfactants and comprises

* either a linear or branched aliphatic chain of 3 to 10 carbon atoms, possibly bearing heteroatoms, bearing an acidic function such as sulfuric, sulfonic, carboxylic or phosphoric acid and possessing a condensed aliphatic chain bearing at least 1 to 6 saturated rings of 5 or 6 carbon atoms,

* or a linear or branched aliphatic chain of at least 8 carbon atoms, preferably from 10 to 18 carbon atoms, this chain being substituted, where appropriate, by one (or several) ring(s) or aromatic heterocycle(s), the said chain or this (or these) ring(s) or aromatic heterocycle (s) being substituted by an acidic function such as a carboxylic, sulfonic or phosphoric acid, . or is a negatively charged aromatic derivative bearing at least two condensed aromatic rings such as naphthalene, or an aromatic ring condensed with an aromatic heterocycle such as quinoline, or two condensed aromatic heterocycles, at least one of the rings bearing an acidic function such as a sulfuric, carboxylic, sulfonic or phosphoric acid etc . . . and the other ring, not bearing a function capable of abolishing the hydrophobic character of the whole molecule and, in particular, not bearing a polar charge.

With respect to anionic surfactants, mention may be made of sodium dodecylsulfate, sodium dodecylbenzenesulfonate and sodium cholate.

Negatively charged aromatic derivatives are advantageously selected from the following compounds:

naphthalene 2-carboxylic acid, naphthalene 2-sulfonic acid, 2-amino naphthalene 1-sulfonic acid, 4-hydroxy naphthalene 1-sulfonic acid, 1-amino naphthalene 5-sulfonic acid, Amido Black, Violet acid 17, Coomassie Blue R250, Palatine fast black wan, and preferably:

1-hydroxy naphthalene 2-carboxylic acid, 3-hydroxy naphthalene 2-carboxylic acid.

In the case of the anionic surfactants, the range of effective concentration in the gel is advantageously about $10^{-6}$ to about $10^{-3}$M, and preferably about $10^{-4}$ to about $10^{-3}$M. In the case in which the anionic surfactants are introduced into the biological sample before electrophoresis, their concentration is advantageously about $10^{-4}$M to about $10^{-1}$M and preferably about $10^{-3}$M to about $10^{-2}$M. This concentration is such that the rate of migration of LDL is accelerated more than that of the Lp(a) fraction such that the minimal distance between Lp(a) and the LDL fraction on the gel is at least 3 mm (Lp(a) being situated "behind" the LDL fraction).

With respect to the negatively charged aromatic derivatives, the range of effective concentration in the gel is about $10^{-3}$M to about $10^{-1}$M, and preferably about $10^{-2}$M to about $5.10^{-2}$M, and if they are introduced beforehand into the biological sample, their range of effective concentration is about $10^{-2}$M to about 1M, and preferably about $5.10^{-2}$M to $5.10^{-1}$M.

According to a preferred embodiment of the invention, the compound capable of modifying the electrophoretic mobility of Lp(a) differentially with respect to the other lipoproteins is a neutral surfactant (or neutral detergent).

Preferably, the neutral surfactant is such that it is soluble in the aqueous phase, and is advantageously selected from Triton X100$^R$, Triton X405$^R$, Tween 20$^R$, NP40$^R$ and BRIJ35$^R$.

When they are in the gel, the neutral surfactants are advantageously at a concentration of about $10^{-6}$ to $10^{-3}$M, and preferably $10^{-4}$M to $10^{-3}$M. When they are introduced into the biological sample, prior to electrophoresis, the neutral surfactants are advantageously at a concentration of about $10^{-4}$M to $10^{-1}$M, and preferably $10^{-3}$M to $10^{-2}$M.

According to another embodiment of the invention, the separation of Lp (a) and the various lipoproteins contained in a biological sample is advantageously performed on an electrophoresis gel modified with respect to a standard gel by a mixture of cationic compounds and a neutral detergent. These compounds, capable of modifying the mobility of Lp(a), are added according to the methods previously described in conformity with the different embodiments of the invention.

The relative proportions of the cationic compounds and the neutral detergents are determined by the properties of these constituents, namely their capacity to retard preferentially certain lipoprotein fractions. A sufficient retardation of the VLDL, allowing the Lp(a) to be visualized, can be obtained by using only a cationic compound or a neutral detergent. However, in the case in which very fresh serum is used (one stored for less than 24 h at 4° C.), greater mobility of the VLDL observed requires that a very high concentration of cationic compounds be used; in this case the LDL are retarded to the extent that they remain at the loading point and the ionic strength produced is too high, leading to too long a migration time. In such a case it is advantageous to add a neutral detergent to the cationic compounds.

Similarly, when only a neutral detergent is used with very fresh serum, too great a retardation of the LDL fraction may be observed, which may mask the Lp(a), as may a distortion of the bands. The combined use of cationic compounds and a neutral detergent, in proportions which can be optimized by the person skilled in the art, leads to the desired lipoprotein profile.

The object of the invention is also any gel for electrophoresis characterized in that it contains cations or cationic complexes.

The cations or cationic complexes included in these gels are advantageously selected from those described above.

The invention also relates to any gel for electrophoresis characterized in that it contains molecules which have a hydrophobic moiety and are negatively charged, in particular those selected from the molecules described above.

The invention also relates to any gel for electrophoresis characterized in that it contains neutral surfactants, in particular those selected from the agents described above.

The invention preferably relates to an electrophoresis gel, characterized in that it contains mixtures of cationic compounds and neutral detergents.

The invention relates more particularly to the use of these gels for the implementation of the procedure for the separation of Lp(a) and various lipoprotein fractions contained in a biological sample, such as that described above, by means of electrophoresis.

A particularly preferred gel of the invention is that comprising $Mg^{2+}$ as a cation under the concentration conditions specified above.

Apart from the presence of compounds capable of modifying the electrophoretic mobility of Lp(a) differentially with respect to the other lipoproteins, the gels of the invention are gels finding standard use in the area of electrophoresis, in particular agarose, polyacrylamide or cellulose acetate gels.

The gels of the invention may be prepared by mixing the solution of the compounds mentioned above with a warm solution of the gel, followed by a gel solidification step upon return to room temperature.

The gels of the invention may also be prepared by immersion of a gel in a solution of the above-mentioned compounds for a time sufficient to allow the penetration of the required amount of the abovementioned compound.

The invention also relates to the application of the separation procedure,for Lp(a) described above to the determination of the atheroxenic risk in man associated with the presence of Lp(a) in the organism.

Consequently, another object of the invention is an in vitro method of determining the atherogenic risk associated with the presence of Lp(a), this method being carried out on a biological sample taken from a subject, in particular from serum or plasma, and comprising:

the loading of a suitable quantity of the biological sample in the form of a liquid onto an electrophoresis gel containing at least one compound capable of modifying the electrophoretic mobility of Lp(a) differentially with respect to the other lipoproteins, in particular a gel such as that defined above, or onto a gel prepared immediately beforehand from a standard gel not containing a compound such as that defined above by immersing this standard gel for a sufficient time in a solution of this compound in order that the required amount of the above-mentioned compound penetrates, immersion particularly in a solution containing cations or cationic complexes selected from those mentioned above, or molecules which have a hydrophobic moiety and are negatively charged selected in particular from those mentioned above or neutral surfactants selected in particular from those mentioned above, an electrophoretic migration step, the detection of Lp(a) possibly present in the biological sample, in particular with the aid of a specific stain for lipoproteins such as the stains Sudan Black, Sudan Red, or enzymatic reagents specific for lipids or antibodies directed against the lipoproteins, and in particular against Lp(a).

The invention also relates to a method for the in vitro determination of the atherogenic risk associated with the presence of Lp(a), this method being carried out on a biological sample taken from, a subject, in particular from serum or plasma, and comprising:

the incubation of the biological sample taken with a solution containing molecules which have a hydrophobic moiety and are negatively charged selected in particular from those mentioned above or neutral surfactants, in particular those mentioned above, the loading of a suitable quantity of the biological sample thus treated onto a standard gel for electrophoresis, an electrophoretic migration step, the detection of the Lp(a) possibly present in the biological sample, in particular with the aid of a specific stain for lipoproteins such as the stains Sudan Black, Sudan Red, or enzymatic reagents specific for lipids, or antibodies directed against the lipoproteins, and in particular against Lp(a).

The position of Lp(a), which may be located by means of a specific anti-Lp(a) antibody is, in current practice which makes use of the procedure of the invention, revealed by a specific stain for lipoproteins such as the stains Sudan Black, Sudan Red or enzymatic reagents specific for lipids.

These methods for determining the atherogenic risk advantageously comprise an additional step for the assay of Lp(a), in particular according to the method LAURELL et al., published in Anal. Biochem. (1966) 15: 45–52. The threshold of sensitivity of the diagnostic method of the invention is on the order of 0.15 g/l of plasma Lp(a), the pathological level of Lp(a) being of the order of 0.3 g/l.

In a very useful manner, the procedure according to the invention enables Lp(a) in its native form to be separated from the various lipoproteins present in their native form in the biological sample loaded onto the gel, and does so as a result of electrophoresis followed by revelation by staining, without recourse to the immunoblot procedure. When the procedure according to the invention is performed, Lp(a) is situated between the VLDL and HDL fractions, thus perfectly resolved in a distinct zone of the gel and without tailing (thus lacking background noise).

Furthermore according to the procedure of the invention, the IDL fraction sometimes present in type III hyperlipidemia is situated between the LDL and VLDL and can on no account be confused with Lp(a).

Finally, in the case of old serum samples, the retardation of the VLDL fraction (prebeta) can in no way mask Lp(a) which precedes the VLDL fraction.

Using the electrophoresis procedure on standard gels and as a consequence of the various disadvantages described above it may be pointed out that the densitometric reading of the lipidogram exhibits a lower specificity and sensitivity than the visual examination of the analysis.

The correlation between the Lp(a) values obtained by densitometry on standard gels and an assay procedure for Lp(a) using immunonephelometry is only=0.55 (Clinica Chimica Acta, 188, 1990, p. 71–78).

According to the procedure which we propose, the correlation between the densitometry of the lipidogram and an assay procedure for Lp(a) using electroimmunodiffusion according to Laurell shows a correlation coefficient =0.91 (on 30 Lp(a)-positive sera).

Another object of the invention relates to kits for the implementation of a procedure or a diagnostic method according to the invention, containing:

a gel for electrophoresis, in particular an agarose gel,
one or several solutions of compounds, these compounds being in particular cations or cationic complexes selected in particular from those mentioned above, or negatively charred hydrophobic molecules selected in particular from those mentioned above or neutral surfactants selected in particular from those mentioned above,
the buffer solution(s) necessary for the electrophoretic migration of the lipoproteins in the gel,
reagents making possible the detection of the lipoproteins, including Lp(a), after migration in the gel, in particular the stains Sudan Black, Sudan Red, or enzymatic reagents specific for lipids.

The solution used in the kit is used either to rebuffer the gel,
or is added to the biological sample.

The invention also relates to kits such as those described above comprising:

a gel according to the invention containing at least one compound capable of modifying the electrophoretic mobility of Lp(a) differentially with respect to the other lipoproteins, in particular a gel such as that defined above,
buffer solution(s) necessary for the electrophoretic migration of the lipoproteins in the gel,
reagents making possible the detection of the lipoproteins, including Lp(a), after migration in the gel, in particular the stains Sudan Black, Sudan Red or enzymatic reagents specific for lipids.

Legends to the figures

The composition of the gel was the following:

0.5% agarose, 0.06M Tris, Veronal 0.01M, 0.05M Veronal sodium salt, 0.1% bovine albumin.

39 ml of demineralized water was introduced into a 100 ml Erlenmeyer flask and 0.25 g of agarose was added with magnetic stirring. The mixture was heated to boiling for 5 mn on a hot plate and with continuous stirring. The agarose was then dissolved, giving a perfectly clear solution. The solution was then placed in a thermostatted bath in order to bring its temperature to 50° C.

10 ml of demineralized water was introduced into a 50 ml Erlenmeyer flask and 0.36 g of Tris, 0.092 g of Veronal, 0.515 g of Veronal sodium salt were added with magnetic stirring. After complete dissolution, the solution was brought to 50° C. by being placed in a thermostatted bath.

1 ml of demineralized water and 0.05 g of bovine albumin were introduced into a hemolysis tube. Dissolution was accelerated with the aid of a Vortex. The solution was heated to 50° C.

The concentrated solutions of buffer and bovine albumin were added with stirring to the 100 ml Erlenmeyer flask containing the agarose solution. The mixture was well homogenized and maintained at 50° C.

The gel was then poured. In order to do this, 5 ml of this solution were uniformly distributed on a hydrophilic plastic film of dimensions 10×8 cm.

2) Preparation of the gels shown in FIGS. 2A and 2B

The composition of the gel was the following:

0.5% agarose, 0.06M Tris, 0.01M Veronal, 0.05M Veronal sodium salt, 0.03M magnesium acetate, 0.1% bovine albumin.

The gel was prepared according to the same protocol as that for FIGS. 1A and 1B, with the difference that 0.322 g of magnesium acetate tetrahydrate was added to the concentrated buffer solution.

3) Migration conditions

The fresh sera were loaded at 2.5 cm intervals on the edge of the gel next to the cathode (3 µl deposits).

The migration was carried out in a buffer consisting of 0.06M Tris, 0.01M Veronal, 0.05M Veronal sodium salt at 50 V for 45 mn.

In the case of FIGS. 1A and 1B, the time of migration was 45 mn.

In the case of FIGS. 2A and 2B, the time of migration was 1 h.

After migration, the gel was dried completely and stained with a lipid stain (Sudan Black) (FIGS. 1A and 2A), or subjected to immunofixation with a specific antiserum directed against Lp(a) (FIGS. 1B and 2B).

EXAMPLE II

Description of the Operations Underlying FIG. 6

The gel is identical with that of FIG. 4. A pre-run of one hour at 50 V was carried out in the direction indicated in the Figure. During this pre-run, the anion was displaced toward the anode such that it was removed from the cathodic part of the gel.

A single sample of a serum containing Lp(a) was then applied over the total length of the gel and migration was carried out in the direction perpendicular to that of the pre-run for 45 mn. The lipoproteins were then stained with Sudan Black.

EXAMPLE III

Comparison of the Distances of Migration of the Lipoprotein Fractions in the Different Gels d distance of migration in the gel containing the compound
$d_T$ distance of migration in the reference gel
1) Gel of the invention with 0.03M magnesium acetate (gel shown in FIG. 4):

| Lipoprotein fraction | HDL | VLDL | LDL | Lp(a) |
|---|---|---|---|---|
| $\frac{d}{d_T}$ | 0.75 | 0.61 | 0.5 | 0.96 |

2) Gel of the invention containing 0.026M 1-hydroxy naphthalene 2-carboxylic acid (gel shown in FIG. 4):

| Lipoprotein fraction | HDL | VLDL | LDL | Lp(a) |
|---|---|---|---|---|
| $\frac{d}{d_T}$ | 1.42 | 1.9 | 2.67 | 1.1 |

EXAMPLE IV

A standard gel of the same composition as that obtained in Example I corresponding to FIGS. 1A and 1B was subjected, prior to the loading of the samples, to pre-electrophoresis in the migration buffer: 0.06M Tris, 0.01M Veronal, 005M Veronal sodium salt, 0.1% bovine albumin, 1-hydroxy naphtalene 2-carboxylic acid having been added to the buffer in the cathode reservoir to give a concentration of 0.026M.

After migration for 30 at 50 volts, corresponding to a potential gradient of about 6 V/cm, the 1-hydroxy naphtalene 2-carboxylic acid had penetrated 40 mm into the gel from the cathode reservoir. The samples was then loaded in this zone, for example at 30 mm from the edge of the gel next to the cathode and the migration of the samples was then allowed to proceed using the same buffers for 45' at a potential of 50 V.

The lipidograms obtained are identical with those produced in the gel shown in FIG. 4.

EXAMPLE V

A standard gel of the same composition as that used in Example I shown in FIGS. 1A and 1B was subjected, prior to the loading of the samples, to preelectrophoresis in the migration buffer: 0.6M Tris, 0.01M Veronal, 0.05M Veronal sodium salt, 0.1% bovine albumin, $5\times10^{-2}$M magnesium acetate having been added to the buffer in the anode reservoir.

After migration for 45' at 50 V, corresponding to a potential gradient of about 6V/cm, the $Mg^{2+}$ ions have penetrated 40 mm into the gel from the anode reservoir.

The samples were then loaded in a zone of the gel in front of the $Mg^{2+}$ ions front situated, for example, at 45 mm from the gel next to the anode. The migration was then performed using the same buffers for 1 h at a potential of 50 V. The profile obtained was similar to that produced in the gel in FIGS. 2A and 2B and shows, in particular, the Lp(a) fraction preceding the VLDL fraction but a better separation of the LDL fraction from the loading point of the samples.

We claim:

1. A procedure for the separation of native Lp(a) and various native lipoproteins contained in a biological sample comprising the steps of: electrophoresing the biological sample, wherein the electrophoretic migration of the native lipoproteins is carried out under conditions such that the electrophoresis gel and/or the biological sample contains one or more agents capable of modifying the electrophoretic mobility of native Lp(a) differentially with respect to that of the other native lipoproteins, wherein said one or more agents are selected from a cation or a cationic complex, a molecule having a hydrophobic moiety and is negatively charged or a neutral surfactant.

2. The procedure according to claim 1, wherein the agent capable of modifying the electrophoretic mobility of Lp(a) differentially with respect to that of the other lipoproteins is selected from a cation or a cationic complex, the hydroxide of which is not precipitated or is partially precipitated in the range of about pH 8 to about pH 9 such that there at least $10^{-3}$ moles/l of unprecipitated cation or cationic complex in the gel for electrophoresis.

3. The procedure according to claim 1, wherein the cation has an oxidation state greater than or equal to 2 and is selected from columns IIa, IIIa or IIIb of the periodic table.

4. The procedure according to claim 1, wherein the cation is $Mg^{2+}$, $Ca^{2+}$, $Ba^{2+}$, $Sr^{2+}$, $Mn^{2+}$, $Be^{2+}$, $Al^{3+}$, $La^{3+}$, $Ce^{3+}$, $In^{3+}$, or $Y^{3+}$.

5. The procedure according to claim 1, wherein the cationic complex comprises a moiety of $NH_4^+$ or is $(NH_4^+)_2Fe^{2+}$ or $NH_4^+Fe^{3+}$.

6. The procedure according to claim 1, wherein the concentration of the molecule having a hydrophobic moiety and is negatively charged in the gel is about $10^{-3}$M to $10^{-1}$M, or if they are introduced beforehand into the biological sample, the concentration is about $10^{-2}$ to about 1M.

7. The procedure according to claim 1, wherein the said molecule having a hydrophobic moiety and is negatively charged is:

an anionic surfactant comprising a linear or branched aliphatic chain of 3 to 10 carbon atoms, an acidic functional group, and a condensed aliphatic chain containing at least 1 to 6 saturated rings of 5 or 6 carbon atoms;

an anionic surfactant comprising a linear or branched aliphatic chain of 3 to 10 carbon atoms containing heteroatoms, an acidic functional group, and a condensed aliphatic chain containing at least 1 to 6 saturated rings of 5 to 6 carbon atoms;

an anionic surfactant comprising a linear or branched aliphatic chain of at least 8 carbon atoms substituted by an acidic functional group;

an anionic surfactant comprising a linear or branched aliphatic chain of at least 8 carbon atoms substituted by an acidic functional group and substituted with at least one ring or aromatic heterocycle;

an anionic surfactant comprising a linear or branched aliphatic chain of at least 8 carbon atoms substituted by an acidic functional group and substituted with a least one ring or aromatic heterocycle wherein the ring or aromatic heterocycle is substituted by an acidic functional group;

an anionic surfactant comprising a linear or branched aliphatic chain of at least 8 carbon atoms substituted with at least one ring or aromatic heterocycle wherein the ring or aromatic heterocycle is substituted by an acidic functional group; or an negatively charged aromatic derivative that contains at least two condensed aromatic rings, at least one of the rings bearing an acidic functional group wherein the ring lacking the acidic functional group does not abolish the hydrophobic character of the whole compound and does not bear a polar charge.

8. The procedure according to claim 7 wherein the derivative that comprises at least two condensed aromatic rings comprises as aromatic rings naphthalene, an aromatic ring condensed with an aromatic heterocycle, quinoline, or two condensed aromatic heterocycles.

9. The procedure according to claim 7, wherein the concentration of the anionic surfactant in the electrophoresis gel is of the order of $10^{-6}$M to $10^{-3}$M, or if they are introduced beforehand into the biological sample, the concentration is of the order of $10^{-4}$ to $10^{-1}$M.

10. The procedure according to claim 7, wherein the anionic surfactant is sodium dodecylbenzenesulfonate or sodium cholate.

11. The procedure according to claim 1 wherein said molecule having a hydrophobic moiety and is negatively charged comprises as an acidic functional group a sulfuric acid, a sulfonic acid, a carboxylic acid, or a phosphoric acid.

12. The procedure according to claim 1, wherein said molecule having a hydrophobic moiety and is negatively charged is naphthalene 2-carboxylic acid, naphthalene 2-sulfonic acid, 2-amino naphthalene 2-sulfonic acid, 4-hydroxy naphthalene 1-sulfonic acid, 1-amino naphthalene 5-sulfonic acid, Amido Black, Violet Acid 17, Coomassie Blue R250, or Palatine fast black wan.

13. The procedure according to claim 1, wherein the agent capable of modifying the electrophoretic mobility of Lp(a) differentially with respect to other lipoproteins is a neutral surfactant.

14. The procedure according to claim 13, wherein the neutral surfactant is Triton X100$^R$, Triton X405$^R$, Tween 20$^R$ or BRIJ35$^R$.

15. The procedure according to claim 13, wherein the concentration of the neutral surfactant in the electrophoresis gel is on the order of $10^{-6}$M to $10^{-3}$M, or if they are introduced beforehand into the biological sample, the concentration is on the order of $10^{-4}$M to $10^{-1}$M.

16. A procedure for the separation of native Lp(a) and various native lipoproteins contained in a biological sample comprising the step of: electrophoresing the biological sample wherein the biological sample contains native LDL, VLDL or HDL and an agent makes it possible to separate a native Lp(a) fraction from the native VLDL or LDL fractions in a biological sample either maintaining separation of the native HDL, LDL and VLDL, or not maintaining the separation of native HDL, LDL and VLDL, wherein the electrophoretic migration of the lipoproteins is carried out under conditions such that the electrophoresis gel and/or the biological sample contains one or more agents capable of modifying the electrophoretic mobility of native Lp(a) differentially with respect to that of the other native lipoproteins, wherein said one or more agents are selected from a cation or a cationic complex, a molecule having a hydrophobic moiety is negatively charged, or a neutral surfactant.

* * * * *